US009919163B2

(12) United States Patent
Khan et al.

(10) Patent No.: US 9,919,163 B2
(45) Date of Patent: Mar. 20, 2018

(54) METHODS, SYSTEMS AND COMPUTER READABLE STORAGE MEDIA FOR DETERMINING OPTIMAL RESPIRATORY PHASE FOR TREATMENT

(71) Applicants: EMORY UNIVERSITY, Atlanta, GA (US); GEORGIA TECH RESEARCH CORPORATION, Atlanta, GA (US)

(72) Inventors: Mohammad Khurram Khan, Atlanta, GA (US); Jerome Landry, Atlanta, GA (US); Lei Zhu, Atlanta, GA (US)

(73) Assignees: Emory University, Atlanta, GA (US); Georgia Tech Research Corporation, Atlanta, GA (US)

(*) Notice: Subject to any disclaimer, the term of this patent is extended or adjusted under 35 U.S.C. 154(b) by 217 days.

(21) Appl. No.: 14/623,999

(22) Filed: Feb. 17, 2015

(65) Prior Publication Data
US 2015/0231410 A1 Aug. 20, 2015

Related U.S. Application Data

(60) Provisional application No. 61/940,386, filed on Feb. 15, 2014.

(51) Int. Cl.
*A61N 5/10* (2006.01)
(52) U.S. Cl.
CPC ......... *A61N 5/1037* (2013.01); *A61N 5/1068* (2013.01)
(58) Field of Classification Search
CPC .. A61N 5/1037; A61N 5/1068; A61N 5/1067; A61N 2005/1061; A61N 5/1031;
(Continued)

(56) References Cited

U.S. PATENT DOCUMENTS 6,546,073 B1 * 4/2003 Lee ............... A61N 5/1031 378/65
6,937,696 B1 * 8/2005 Mostafavi ......... A61B 5/7292 378/65

(Continued)

FOREIGN PATENT DOCUMENTS

WO 2011/153639 A2 12/2011

OTHER PUBLICATIONS

Cahill et al. "A Demons Algorithm for Image Registration with Locally Adaptive Regularization." Medical Image Computing and Computer-Assisted Intervention, 2009. 12 (Pt 1): 574-81.

(Continued)

*Primary Examiner* — Irakli Kiknadze
(74) *Attorney, Agent, or Firm* — Emory Patent Group

(57) ABSTRACT

Methods, systems and computer-readable storage media relate to determining optimal treatment information. The methods may include determining a dose distribution for one or more target regions by applying a deformation parameter to a treatment plan dose distribution for a subset of a plurality of phases. The method may also include determining one or more dose parameters based on the dose distribution for the subset of the plurality of phases. The one or more dose parameters may represent a motion of the dose distribution over the plurality of phases for each region. The method may further include determining optimal treatment information based on the one or more dose parameters. The optimal treatment information may include optimal phase and associated dose distribution and the optimal phase may be a phase having a minimum total dose for the one or more target regions.

20 Claims, 5 Drawing Sheets

(58) Field of Classification Search
CPC .............. A61N 5/1042; A61N 5/1048; A61N 2005/1072; A61N 5/103; A61N 5/1038; A61N 5/1039; A61N 5/107; A61N 5/1071; A61N 5/1077; A61N 5/1075; A61N 2005/1076; A61N 5/1064; A61N 2005/1054; A61N 5/1036; A61N 5/1045; A61N 5/1047; A61B 6/4085; A61B 6/4458; A61B 6/4464; A61B 6/486; A61B 6/5205; A61B 6/5264; A61B 6/541; A61B 6/538; A61B 6/481; A61B 6/508; A61B 6/032; A61B 6/4441; A61B 6/504; A61B 6/542; A61B 5/055; A61B 6/08; A61B 6/461; A61B 6/488; A61B 6/50; A61B 6/503; A61B 6/507; A61B 6/5211; A61B 6/5288; C40B 30/10; C40B 60/12; G01T 1/04; G01T 1/204; G06F 19/3437; G06F 19/3481; G06F 3/04815; G21K 1/046
USPC .......................................... 378/4, 19, 62, 65
See application file for complete search history.

(56) References Cited

U.S. PATENT DOCUMENTS

| | | | |
|---|---|---|---|
| 8,767,917 B2* | 7/2014 | Ruchala | A61N 5/103 378/65 |
| 8,819,591 B2* | 8/2014 | Wang | G06F 19/3437 715/850 |
| 2009/0316858 A1* | 12/2009 | Nord | A61N 5/1031 378/65 |
| 2012/0136194 A1 | 5/2012 | Zhang et al. | |

OTHER PUBLICATIONS

Thornqvist et al. "Propagation of target and organ at risk contours in radiotherapy of prostate cancer using deformable image registration." Ada Ocnologica, 2010. 49(7): 1023-1032.

Wang et al. "Validation of an accelerated 'demons' algorithm for deformable image registration in radiation therapy." Physics in Medicine & Biology, 2005. 50:2887-2905.

Wang et al. "Motion Effects on Organ Dose in Respiratory Gated Stereotactic Body Radiation Therapy." Presentation SU-E-J-89 Sunday 3:00-6:00 PM. AAPM 2014 56th Annual Meeting & Exhibition, Jul. 20-24, 2014, Austin, TX [retrieved from the Internet <URL: http://www.aapm.org/meetings/2014am/PRAbs.asp?mid=90&aid=24979> on Jul. 18, 2017].

Wang et al. "Motion Effects on Organ Dose in Respiratory Gated Stereotactic Body Radiation Therapy." Poster presented at AAPM 2014 56th Annual Meeting & Exhibition, Jul. 20-24, 2014, Austin, TX.

Wang et al. "Motion Effects on Organ Dose in Respiratory Gated Stereotactic Body Radiation Therapy." International Journal of Radiation Oncology • Biology • Physics, 2014. 90(1):S906.

* cited by examiner

|  | Dose (Gy) | | | | Volume(%) |
|---|---|---|---|---|---|
| Criterion | < 0.1 cc | <1 cc | <3 cc | <5 cc | Dose>5Gy |
| Planned | 44.58 | 35.67 | 23.86 | 17.52 | 28.18 |
| Optimized | 42.79 | 29.91 | 14.33 | 6.631 | 18.38 |

FIGURE 5

METHODS, SYSTEMS AND COMPUTER READABLE STORAGE MEDIA FOR DETERMINING OPTIMAL RESPIRATORY PHASE FOR TREATMENT

CROSS REFERENCE TO RELATED APPLICATION

This application claims priority to Provisional Application Ser. No. 61/940,386 filed Feb. 14, 2014, which is hereby incorporated by reference in its entirety.

BACKGROUND

The success of radiotherapy, such as stereotactic body radiation therapy (SBRT), generally relies on the accuracy of the localization of the tumor and surrounding organs at risk (OAR). Often, this is based on a physician's judgment. Conventionally, a physician subjectively determines a treatment phase for which the treatment plan is based from the obtained 4D Computer-Tomography (CT) image data and associated respiratory gating signals from external surrogates. The radiation therapy is then delivered to the tumor only during the physician selected treatment phase. However, errors in selecting the treatment phase can have devastating consequences for the surrounding normal tissue, for example, by resulting in severe toxicity from the radiation treatment.

SUMMARY

Thus, there is a need for automatically determining an optimal treatment phase for delivering radiation therapy.

The disclosure relates to systems, methods, and computer-readable media storing instructions for determining optimal treatment information based on respiration motion of a patient.

In some embodiments, a method may include determining a dose distribution for one or more target regions by applying a deformation parameter to a treatment plan dose distribution for a subset of a plurality of phases. The method may also include determining one or more dose parameters based on the dose distribution for the subset of the plurality of phases. The one or more dose parameters may represent a motion of the dose distribution over the plurality of phases for each region. The method may further include determining optimal treatment information based on the one or more dose parameters. The optimal treatment information may include optimal phase and associated dose distribution and the optimal phase may be a phase having a minimum total dose for the one or more target regions.

In some embodiments, a system may include at least one processor; and a memory. The system may be configured to cause determining a dose distribution for one or more target regions by applying a deformation parameter to a treatment plan dose distribution for a subset of a plurality of phases. The system may also be configured to cause determining one or more dose parameters based on the dose distribution for the subset of the plurality of phases. The one or more dose parameters may represent a motion of the dose distribution over the plurality of phases for each region. The system may further be configured to cause determining optimal treatment information based on the one or more dose parameters. The optimal treatment information may include optimal phase and associated dose distribution and the optimal phase may be a phase having a minimum total dose for the one or more target regions.

In some embodiments, a non-transitory computer-readable storage medium may include instructions for determining a dose distribution for one or more target regions by applying a deformation parameter to a treatment plan dose distribution for a subset of a plurality of phases. The instructions may also include determining one or more dose parameters based on the dose distribution for the subset of the plurality of phases. The one or more dose parameters may represent a motion of the dose distribution over the plurality of phases for each region. The instructions may further include determining optimal treatment information based on the one or more dose parameters. The optimal treatment information may include optimal phase and associated dose distribution and the optimal phase may be a phase having a minimum total dose for the one or more target regions.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

FIG. 5 shows an example of a table of a comparison of clinical endpoints.

DESCRIPTION OF THE EMBODIMENTS

Figure 1:
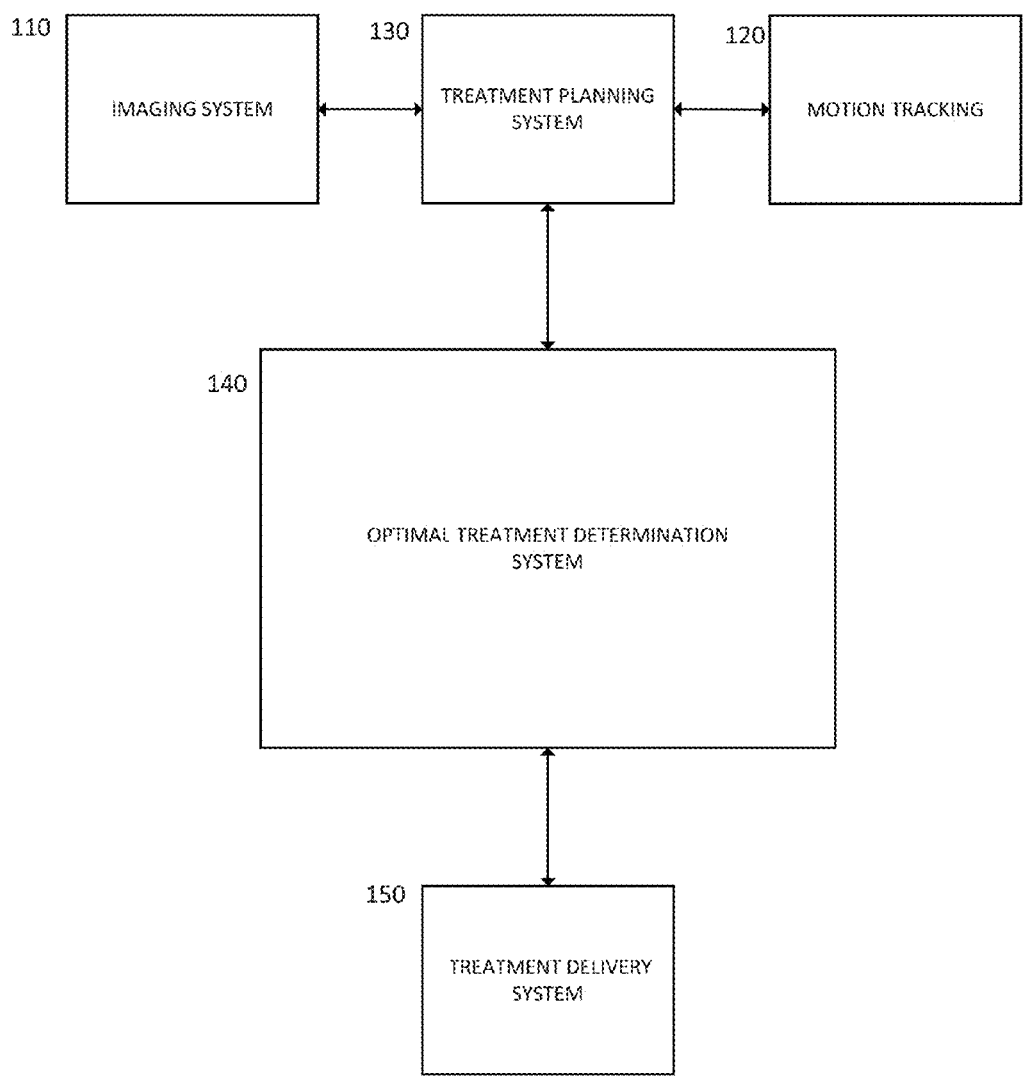
FIG. 1 shows a block diagram illustrating a system according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The disclosed methods, systems, and computer-readable media relate to determining optimal treatment information based on respiration (motion) of a patient. The optimal treatment information can include optimal (respiratory) phase(s) for delivery of the radiation treatment and associated treatment dose. The disclosure optimizes the treatment phase for maximization of OAR sparing. The disclosure relates to generating delivered dose distributions and comparing the dose sparing on OARs to determine the optimal phase. The optimal phase can be determined according to the pre-defined clinical criteria on organ specific and treatment specific dose volume histograms (DVH). The disclosure thereby removes primarily subjective decisions of treatment by the physician and reduces any possible errors resulting therefrom.

Treatment can also be improved because the treatment phase can be specific to the patient, for example, the patient's respiratory motion and organ motion due to respiration. It thus can potentially reduce the dose to surrounding areas, normal dose and the risks of secondary cancers while maintaining acceptable doses to the target.

Additionally, the disclosed methods, systems, and computer-readable media address the deficiencies associate with other methods that can determine an optimal treatment plan. For example, inverse treatment planning can determine an optimal treatment plan by comparing the simulated treatment performance on each phase. However, the inverse planning work for different gating phases, including organ contouring, dose calculation and dose inverse optimization, can be manpower and computationally intensive. The disclosure can expedite the planning process without sacrificing accuracy in determining optimal treatment information.

The disclosed methods, systems, and computer-readable media are discussed with respect to one or more target regions. The target region can be an organ and/or surrounding structure or organ, and/or a tumor within an organ and/or surrounding structure, or a combination thereof intended to receive treatment. For example, if the target region is the pancreas, the surrounding target regions (e.g., the organs at risk) can include duodenum, stomach, and/or liver.

FIG. 1 shows an example of a system 100 capable of determining optimal treatment information according to embodiments. As shown in FIG. 1, the system may include a medical imaging system 110, a motion tracking system 120, treatment planning system 130, an optimal treatment determination system 140, and a treatment delivery system 150.

In some embodiments, the imaging system 110, which may be part of the treatment delivery system 150, may be any imaging modality that has a capability of generating image data that provides 4D visualization of a body and internal body motion. The medical imaging system 110 may include but is not limited to positron emission tomography (PET) imaging and single positron emission computed tomography (SPECT) imaging, computed tomography (CT) or magnetic resonance imaging (MRI) imaging modality, and a combined imaging modality, such as a PET/CT or SPECT/CT imaging system.

The motion monitoring system 120 can be connected to the imaging system 110 and/or the treatment delivery system 150. The motion monitoring system 120 can be any motion system capable of generating motion data. The motion tracking system 120 may be configured to track in real-time a target region relative to a machine isocenter or another external reference frame outside of the patient to determine motion data during treatment planning, set up, treatment (radiation) sessions by the treatment delivery system 150, and/or other times of the radiation therapy process. The motion tracking system 120 may be configured to obtain motion data via any suitable technique, such as by tracking one or more internal or external surrogates or markers that are positioned near the target region. The external surrogates may be, for example, infrared surrogates. The motion data may relate to respiratory motion as well as other organ motion data.

The motion data obtained by the motion monitoring system 120 may be associated with the image data of the imaging system 110 to generate gated image data of different phases for a cycle. For example, the motion data detecting the patient's breathing, and the image data and a breathing signal may be collected at the same time. The collected images can be marked with time information in the breathing cycle (i.e., phase), and then based on the respective phases, all of the images can respectively divided into groups. The images can be reconstructed, wherein the three-dimensional images of the phases form a three-dimensional image sequence over time, e.g., 4D-CT image data. For example, for a 4D-CT system, the motion data caused by respiration may be measured by a pneusometer, infrared photographic equipment, or a pressure sensor.

In some embodiments, the treatment plan generation system 130 may be configured to generate a treatment plan based on the gated image data. The treatment plan may include information, such as the defined contours of the one or more target regions, associated dose distribution, the gated image data generated by the imaging system 110 and/or the motion tracking system 120. By way of example, a physician may view the gated image data for one respiratory cycle and define the contours of the one or more target regions. In other example, the treatment plan generation system 130 may automatically define the contours of the one or more target regions. The dose distribution doses to the target region(s) may be based on the determined patient specific treatment planning margins (e.g., provided by the physician). The treatment plan generation system 130 may be any treatment delivery system. The treatment plan generation system 130, for example, may include but is not limited to Pinnacle, Eclipse, Monte-Carlo, as well as others.

By way of example, from the 4D CT phases (0-90), the physician may select a phase (e.g., 30-70) to treat, which will allow for creation of target region (e.g., tumor) contours over which the physician may want to treat/gait the treatment machine. By way of another example, a physician can also create an "average" representation of the entire tumor motion using all of the phases of the 4D CT image data set (i.e., maximum intensity projection (MIP) over all phases).

The optimal treatment determination system 140 may be configured to generate optimal treatment information from the treatment plan information generated by the treatment planning system 130. The optimal treatment information may include one or more optimal treatment (respiratory) phase for delivery of the radiation treatment and associated treatment dose. In some embodiments, the optimal treatment phase may include an optimal treatment phase for each region (e.g., corresponding to the voxels confined with the defined contours of each region) and/or each voxel. The optimal treatment phase may correspond to the (respiratory) phase having a having a minimum total dose (value) for a region and/or minimum dose (value) for a voxel.

The optimal treatment determination system 140 can be configured to determine one or more optimal treatment phases by generating dose distributions for the one or more target regions based on at least respiratory motion of the patient. The optimal treatment determination system 140 can be configured to generate dose distributions for each region based on one or more deformation parameters and determine the optimal treatment phase based on one or more dose parameters. The one or more deformation parameters may represent a movement of the target region(s) (i.e., voxels associated with one or more target regions) due to respiration at different phases. The one or more dose parameters may represent motion of the dose distribution due to one or more target regions over the phases.

The treatment delivery system 150 may be configured to control the treatment to the target region according to the treatment parameters provided in a treatment plan. For example, the treatment delivery system 150 may be configured to deliver a treatment (e.g., a treatment beam) having the dose(s) and during the optimal phase(s) provided in the optimized treatment plan generated by the optimized treatment determination system 140. The treatment delivery system 150 may be any device configured to deliver any therapeutic or diagnostic treatment, such as radiotherapy, to tissue of the target region and to control the delivery of the treatment according to treatment parameters and/or having a gated treatment mode.

For example, the treatment delivery system 150 may be any radiation treatment system, for example, capable of external beam radiation therapy. The radiation treatment system may include a radiation source (e.g., an accelerator) configured to generate radiation treatment beam according to treatment parameters and motion signal and a multileaf Collimator (MLC) assembly configured to shape or modulate the output of the radiation source. For example, for radiotherapy, the treatment delivery can generally represent any variable of a treatment, such as radiation beam, the movement of the MLC apertures, and the movement of treatment couch, collimator and/or machine gantry, or any combination thereof. The treatment delivery system 150 may include but is not limited to a body radiotherapy system, such as a stereotactic body radiotherapy (SBRT) system, intensity modulated radiation therapy (IMRT), volumetric modulated arc therapy (VMAT), and proton radiotherapy.

In some embodiments, the system 100 may include a different set of systems or modules, including additional systems or modules, including fewer systems or modules, or sets in which the functionality of the systems or modules is divided or consolidated. In some embodiments, the system 100 may include a different set of systems or modules, including additional systems or modules, including fewer systems or modules, or sets in which the functionality of the systems or modules is divided or consolidated. For example, the optimal treatment determination system 140 may be a part of the treatment planning system 130 and/or the treatment delivery system 150.

In some embodiments, the modules and/or systems of the system 100 may be connected to a data network, a wireless network, or any combination thereof. In some embodiments, any of the modules and/or systems of the system 100 may be at least in part be based on cloud computing architecture. In some embodiments, the modules and/or systems may be applied to a self-hosted private cloud based architecture, a dedicated public cloud, a partner-hosted private cloud, as well as any cloud based computing architecture.

Figure 2:
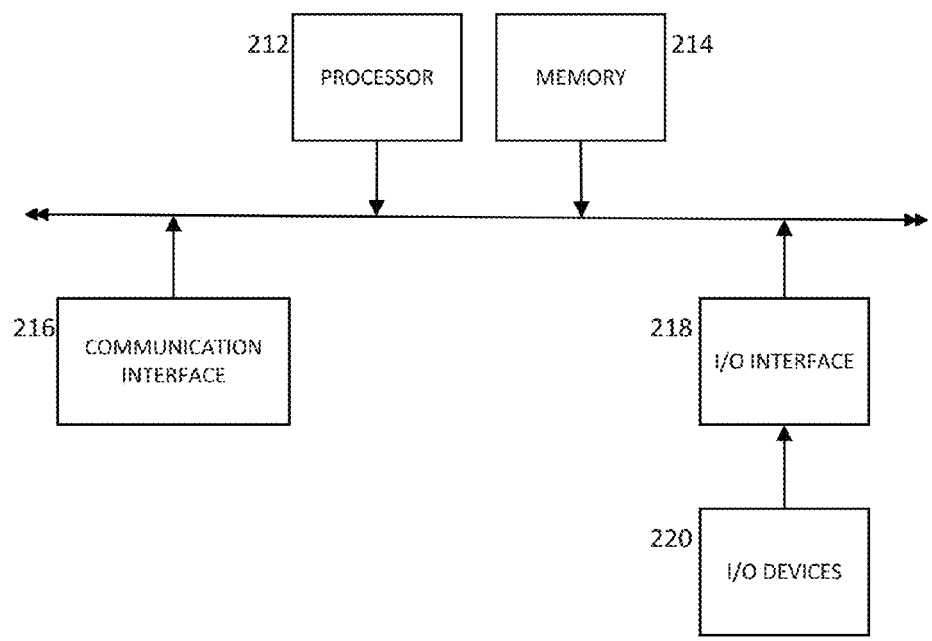
FIG. 2 shows a block diagram illustrating an example of a computing system.

One or more of the modules and/or systems of system 100 may be and/or include a computer system and/or device. FIG. 2 is a block diagram showing a computer system 200. The modules of the computer system 200 may be included in at least some of the systems and/or modules, as well as other devices of system 100.

The systems may include any number of modules that communicate with other through electrical or data connections (not shown). In some embodiments, the modules may be connected via a wired network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radiofrequency network, or another similarly functioning wireless network.

It is also to be understood that the systems may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

In some embodiments, the modules provided within the systems may be time synchronized. In further embodiments, the systems may be time synchronized with other systems, such as those systems that may be on the medical facility network.

The system 200 may be a computing system, such as a workstation, computer, or the like. The system 200 may include one or more processors 212. The processor(s) 212 (also referred to as central processing units, or CPUs) may be any known central processing unit, a processor, or a microprocessor. The CPU 212 may be coupled directly or indirectly to one or more computer-readable storage media (e.g., memory) 214. The memory 214 may include random access memory (RAM), read only memory (ROM), disk drive, tape drive, etc., or a combinations thereof. The memory 214 may be configured to store programs and data, including data structures. In some embodiments, the memory 214 may also include a frame buffer for storing data arrays.

The CPU 212 may be configured to determine individualized treatment margins. In some embodiments, the CPU 212 may be capable of performing the data processing and/or generation of treatment plan. In other embodiments, the system may include a separate CPU for performing the data processing and/or generation of treatment plan.

In some embodiments, another computer system may assume the data analysis or other functions of the CPU 212. In response to commands received from the input device, the programs or data stored in the memory 214 may be archived in long term storage or may be further processed by the processor and presented on a display.

In some embodiments, the system 210 may include a communication interface 216 configured to conduct receiving and transmitting of data between other modules on the system and/or network. The communication interface 216 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 210 may include an input/output interface 218 configured for receiving information from one or more input/output devices 220 (e.g., a keyboard, a mouse, and the like) and/or conveying information to one or more output devices 240 (e.g., a printer, a CD writer, a DVD writer, portable flash memory, etc.). In some embodiments, the one or more input devices 220 may configured to control, for example, the generation of the optimal treatment information, display of the optimal treatment information on a display, printing of the optimal treatment information by a printer interface, among other things.

Figure 3:
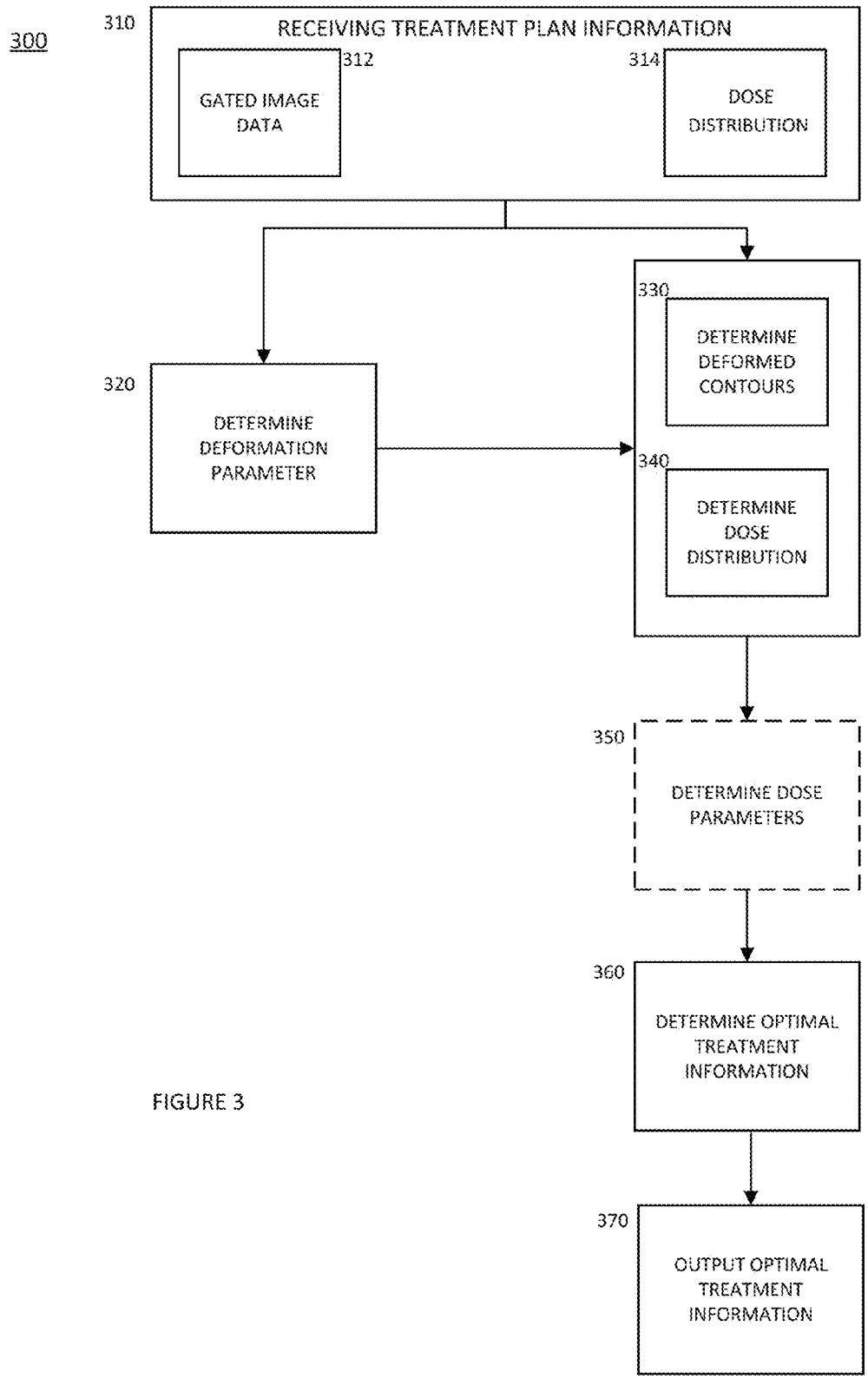
FIG. 3 shows a method of determining optimal treatment information according to embodiments.

FIG. 3 illustrates a method 300 for determining optimal treatment information according to embodiments. The system for carrying out the embodiments of the methods disclosed herein is not limited to the systems shown in FIGS. 1 and 2. Other systems may be used.

The methods of the disclosure are not limited to the steps described herein. The steps may be individually modified or omitted, as well as additional steps may be added. It will be also understood that at least some of the steps may be performed in parallel.

Unless stated otherwise as apparent from the following discussion, it will be appreciated that terms such as "warping," "registering," "deforming," "mapping," "averaging," "combining," "comparing," "generating," "determining," "obtaining," "processing," "computing," "selecting," "receiving," "summing," "estimating," "calculating," "quantifying," "outputting," "acquiring," "analyzing," "approximating," "continuing," "resuming," "using," "retrieving," "sorting," "transmitting," "causing," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

As shown in FIG. 3, the method 300 may include a step 310 of receiving treatment plan information, for example, from the treatment planning system 120. The treatment plan information may include gated image data 312 with defined contours of the one or more target regions and associated dose distribution 314. In some embodiments, the gated image data may be for one respiratory cycle and the dose distribution maybe for an average of the phases and/or a range of the phases. The gated image data 312 may include a set of gated image data for each phase of the cycle. For example, the cycle may include 10 phases (0, 10, 20, 30 . . . 90). In other examples, the cycle may include more or less phases. The contours and/or dose distribution may be defined for a number of the phases and/or the average gated image data.

In some embodiments, the method 300 may include a step 320 of processing the gated image data 312 to determine a deformation parameter for each phase comparison. For example, the phase comparison may include a comparison of each voxel of the set of images at phase 0 to that voxel of each set of images at each remaining phase (e.g., 10, 20, 30, 40 . . . 90). The deformation parameter may represent a movement of each voxel associated with one or more target regions and/or a movement of each region due to respiration at different phases. The deformation parameter, for example, may include a deformation field for each voxel and/or each region. In some embodiments, the optimal treatment determination system 140 may determine the deformation parameter by mapping each voxel or each region of a set of images for one phase onto that voxel or that region of another set of images for a different phase. In other words, the location of each of the image voxels/region of the second image is changed such that the resultant image best matches the first image.

In some embodiments, the deformation parameter(s) may be determined by Demons registration. Using Demons registration, the deformation parameter(s) may relate to the vector difference (M). For example, the deformation parameter (M) may be defined by $M(x,y,z)=V'(x,y,z)-V(x,y,z)$, where $V(x,y,z)$ denote the voxel location vector for the voxel on the original image located at (x,y,z) (e.g., phase 10). After deformable registration (e.g., with respect to phase 0 and phase 10), the voxel is moved to a different location, specified by a different vector $V'(x,y,z)$. In other embodiments, the deformation parameters may be determined by other methods, for example, a Monte-Carlo type approach.

The method 300 may include a step 330 of determining contours for the one or more target regions for each phase by applying each deformation parameter to the one or more defined target regions provided in the treatment plan information and a step 340 of determining dose distribution for the one or more target regions for a subset of the plurality of phases by applying the deformation parameter to the treatment plan dose distribution for one or more phases of the plurality of phases. The steps 330 and 340 may be performed in parallel or in sequential.

In some embodiments, the step 330 may include propagating the defined contours from the phase provided in the treatment plan by applying the deformation parameter to the other phases. For example, the contours for each region provided in the treatment plan information in step 310 may be determined on averaged gated image data (e.g., the phases are averaged) and by applying the deformation factor, the contours for each region can be determined for all phases. In some embodiments, the deformed contours can be determined by warping the contours with the deformation parameter for each phase and for each contour. In this way, the movement (e.g., deformation and/or rotation) of the regions under respiration motion can be determined.

In some embodiments, the step 340 may include determining the dose distribution for the deformed contours of the one or more target regions determined in step 330 from the dose distribution provided in the treatment plan. In some embodiments, the step 340 may include calculating the dose distribution by applying the deformation parameter to the dose distribution values associated with each region (e.g., each voxel associated with each region) provided in the treatment plan.

In some embodiments, in step 340, the deformed dose distribution may be determined for a subset of the phases. The subset may correspond to one or more phases. For example, the dose distribution may be determined for three phases (e.g., 0, 10, and 20). In another example, the dose distribution may be determined for each phase.

In some embodiments, the contours of the one or more target regions for each phase determined in step 330 may be associated with the dose distribution for each phase determined in step 340, respectively.

In some embodiments, the method 300 may include a step 350 of determining one or more dose parameters for each region (e.g., voxel) based on the dose distribution determined in step 340. The one or more dose parameters may represent motion of the dose distribution over the phases of the cycle for (i) the voxels and/or (ii) one or more target regions. In some embodiments, the step 350 may be optional. For example, if the dose distribution is determined for each phase, then the step 350 may be omitted. In another example, for example, if the dose distribution is determined for less than all the phases, then the step 350 may be included. In this way, the number of deformable registrations performed in step 340 and the total computation time can be reduced without reducing the accuracy.

In some embodiments, the one or more dose parameters may include dose amplitude parameter ("A") representing the dose amplitude due to organ motion (e.g., respiratory motion) on a particular phase, mean dose parameter ("b") representing the mean delivered dose over the respiration cycle, and dose variation parameter ("φ") representing the starting phase of the dose variation in a sinusoidal pattern. The one or more dose parameters can be determined based on the dose distribution determined for the subset of the phases in step 340. From those dose parameters, the dose distribution for the other phases (not determined in step 340) may be determined.

In some embodiments, the dose distribution values for the other phases may be determined based on the dose parameters determined for the subset of the phases as a sinusoidal function of the phase. The dose values for each voxel pixels (D) and/or each region for those phases determined in step 340 may be fit to a sinusoidal function. In some embodiments, the sinusoidal function to determine the dose distribution may be represented by the following equation:

$$D(n) = A\sin\frac{2n\pi}{10} + \phi + b \qquad (1)$$

Where D(n) represents the dose value for each voxel and/or region as a sinusoidal function of the phase, n, where A represents the dose amplitude factor, b represents the mean dose parameter, and φ represents the dose variation parameter. In this way, the dose volume can be condensed for efficient clinical use.

In some embodiments, the method 300 may include a step 360 of determining the optimal treatment information based on the dose distribution determined in steps 340 and/or 350. In some embodiments, the optimal treatment information may include optimal treatment phase in which treatment should be delivered for each region and/or voxel and associated dose distribution. The optimal treatment phase may be a phase having a minimum total dose for a region and/or minimum dose for a voxel. In this way, the maximum dose to be delivered to a region can be minimized and thereby the total volume can be reduced.

In some embodiments, the optimal treatment phase may be determined based on one or more dose parameters. For example, the optimal treatment phase for each region can be based on the dose variation parameter (φ) determined in the step 350. In some embodiments, the optimal treatment phase ("p") may be represented by the following equation:

$$\frac{2p\pi}{10} + \phi = -\frac{\pi}{2} \qquad (2)$$

This equation assumes that the initial image data included 10 phases in the cycle. It will be understood that the optimal treatment phase can be determined for more than a different number of phases (e.g., more or less than 10 phases).

Figure 4:
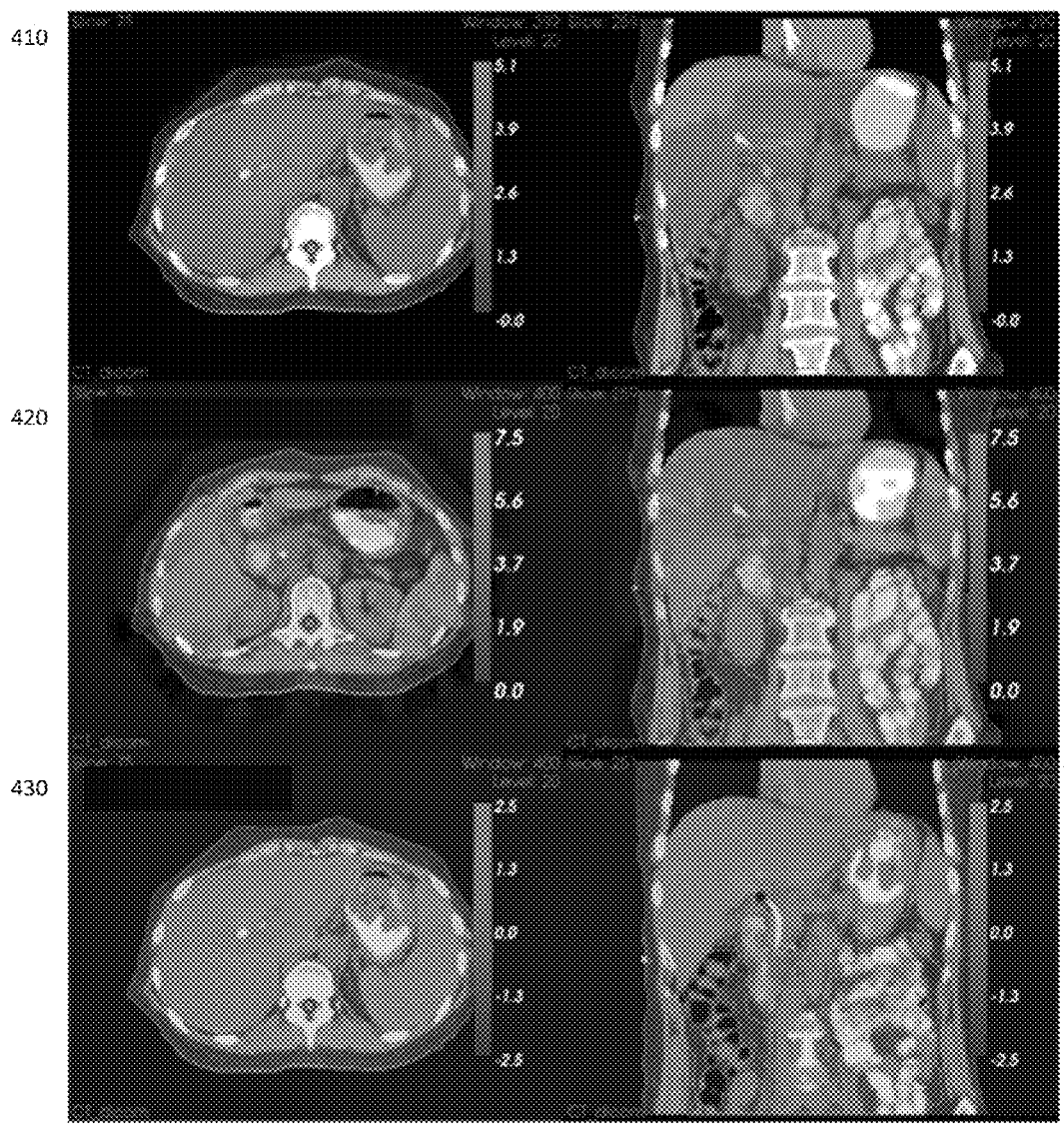
FIG. 4 shows a comparison of examples of image maps for a treatment plan processed according to embodiments.

FIG. 4 shows examples of image maps comparing an initial treatment plan and an optimal treatment plan generated by the disclosed method. Map 410 shows the dose distribution of the initial treatment plan, map 420 shows the spatial distributions of the dose parameters and the optimal phase, and map 430 shows the difference between the phase optimized treatment plan dose distribution shown in map 420 and the initial treatment plan dose distribution shown in map 410.

In some embodiments, the step 350 may include comparing the optimal phase for each region to determine the optimal phase for all regions. The optimal phase for all regions may correspond to phase in which certain (e.g., pre-defined) regions meet a predetermined relationship. For example, the relationship may be the phase in which the dose to the region having normal tissue (e.g., surrounding normal tissue of interest (e.g., duodenum)) is maximally separated from the region including the tumor.

Next, the method 300 may include a step 360 of outputting the optimal treatment information. For example, the optimal treatment information, may be displayed, transmitted, stored, and/or printed. In some embodiments, the optimal treatment information may be displayed, for example, as shown in FIG. 4. In other embodiments, the optimal treatment information may be outputted to a treatment delivery system 150 and the treatment may be caused to be delivered according to the dose distribution and phase provided in the optimal treatment information. For example, using multi-leaf tracking (MLC), the treatment may be only delivered to the regions during those optimal treatment phases provided in the optimal treatment information.

FIG. 5 shows an example of a comparison of several clinical endpoints between an optimal phase determined according to the disclosure and the treatment phases determined in the (initial) treatment plan with respect to the duodenum to treat pancreatic cancer tumors. In this example, the optimal phase corresponds to phase 9 and the initially treatment plan phases correspond to phases 30-70. In the treatment of pancreatic cancer tumors, the goal is generally to minimize a percentage of duodenum (OAR) getting high doses of radiation (in units of Gray, Gy). In the initial treatment plan, the pancreatic cancer was treated to a dose of 45 Gy using the 30-70 respiratory phase defined by a physician. In this non-optimized technique, the dose to less than 0.1 cubic centimeter (i.e. hot spot) to the duodenum was 44.58 Gy. However, if the optimal phase was used (phase 9), the hot spot radiation dose to the duodenum would have been lowered to 42.79 Gy. Similarly, the dose to other clinically relevant endpoints like the percentage of duodenum volume (1 cubic centimeter, 3 cubic centimeter, 5 cubic center) getting radiation particular doses would have also been reduced (35.6 down to 29.9 Gy, 23.8 down to 14.4 Gy, and 17.5 down to 6.6 Gy), respectively with use of an optimized treatment information. Similarly, the volume of the duodenum getting above 5 Gy would have be reduced from 28.18 cubic centimeters down to 18.3 cubic centimeter.

As demonstrated by this table, the disclosure can provide several benefits over the conventional method of determining the treatment phase. For example, the tumor volume representation using maximum tumor intensity projection (MIP) over selected phases can be much smaller because the tumor is defined over only a few phases; the planning target volume (PTV) margin can be reduced because the motion is "frozen" over a few phases; the volume to which the full dose is delivered can be significantly reduced; and the scattered dose to surrounding organs can be reduced. Therefore, the effects from the delivered doses to surrounding organs at risk (OARs) can reduced. Additionally, by determining the optimal phase that efficiently and accurately takes into account the organ motions and changes in organ volumes relative to on another due to respiration, patient treatment efficiency can be increased.

It is to be understood that the embodiments of the disclosure may be implemented in various forms of hardware, software, firmware, special purpose processes, or a combination thereof. In one embodiment, the disclosure may be implemented in software as an application program tangible embodied on a computer readable program storage device. The application program may be uploaded to, and executed by, a machine comprising any suitable architecture. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

In some embodiments, the disclosed methods (e.g., FIG. 3) may be implemented using software applications that are stored in a memory and executed by a processor (e.g., CPU) provided on the system 100. In some embodiments, the disclosed methods may be implanted using software applications that are stored in memories and executed by CPUs distributed across the system 100. As such, any of the systems and/or modules of the system 100 may be a general purpose computer system, such as system 200, that becomes a specific purpose computer system when executing the routine of the disclosure. The systems and/or modules of the system 100 may also include an operating system and micro instruction code. The various processes and functions described herein may either be part of the micro instruction code or part of the application program or routine (or combination thereof) that is executed via the operating system.

If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure. An example of hardware for performing the described functions is shown in FIGS. 1 and 2.

It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method for determining optimal treatment information for a patient, comprising:
   receiving treatment plan information for a patient, the treatment plan information including gated image data of the patient for a plurality of phases with one or more defined target regions and treatment plan dose distribution associated with the one or more target regions;
   processing the treatment plan information to determine a deformation parameter, the deformation parameter representing a movement of each region due to respiration at different phases;
   determining a dose distribution for the one or more target regions by applying the deformation parameter to the treatment plan dose distribution for a subset of the plurality of phases;
   determining one or more dose parameters based on the dose distribution for the subset of the plurality of phases, the one or more dose parameters representing a motion of the dose distribution over the plurality of phases for each region; and
   determining optimal treatment information for the patient based on the one or more dose parameters, the optimal treatment information including an optimal treatment phase and associated dose distribution for each region during the optimal treatment phase, the optimal treatment phase being a phase of the plurality of phases having a minimum total dose for the one or more target regions.

2. The method according to claim 1, wherein the subset of phases corresponds to at least three phases.

3. The method according to claim 1, wherein the one or more dose parameters for each region includes an amplitude parameter, a mean dose parameter, and a dose variation parameter.

4. The method according to claim 3, wherein the amplitude parameter corresponds to a dose amplitude due to motion on a particular phase, the mean dose parameter corresponds to a mean delivered dose over the respiration cycle and the dose variation parameter corresponds to a starting phase of a dose variation in a sinusoidal pattern.

5. The method according to claim 3, wherein the optimal treatment phase is based on the dose variation parameter.

6. The method according to claim 1, further comprising:
   causing a delivery of radiation treatment to the one or more regions during the optimal treatment phase according to the optimal treatment information.

7. The method according to claim 1, wherein the gated image data is 4D-computed tomography (CT) image data.

8. The method according to claim 1, wherein the optimal treatment phase is for all of the one or more defined regions.

9. The method according to claim 1, wherein the one or more dose parameters for each region includes a dose variation parameter that corresponds to a starting phase of a dose variation in a sinusoidal pattern, and wherein the optimal treatment phase is based on the dose variation parameter.

10. A system for determining optimal treatment information for a patient, comprising:
    at least one processor; and
    a memory, wherein the system is configured to cause:
      receiving treatment plan information for a patient, the treatment plan information including gated image data of the patient for a plurality of phases with one or more defined target regions and treatment plan dose distribution associated with the one or more defined target regions;
      processing the treatment plan information to determine a deformation parameter, the deformation parameter representing a movement of each region due to respiration at different phases;
      determining a dose distribution for the one or more target regions by applying the deformation parameter to the treatment plan dose distribution for a subset of the plurality of phases;

determining one or more dose parameters based on the dose distribution for the subset of the plurality of phases, the one or more dose parameters representing a motion of the dose distribution over the plurality of phases for each region; and determining optimal treatment information for the patient based on the one or more dose parameters, the optimal treatment information including an optimal treatment phase and associated dose distribution for each region during the optimal treatment phase, the optimal treatment phase being a phase of the plurality of phases having a minimum total dose for the one or more target regions.

11. The system according to claim 10, wherein the subset of phases corresponds to at least three phases.

12. The system according to claim 10, wherein the one or more dose parameters for each region includes an amplitude parameter, a mean dose parameter, and a dose variation parameter.

13. The system according to claim 12, wherein the amplitude parameter corresponds to a dose amplitude due to motion on a particular phase, the mean dose parameter corresponds to a mean delivered dose over the respiration cycle and the dose variation parameter corresponds to a starting phase of a dose variation in a sinusoidal pattern.

14. The system according to claim 13, wherein the optimal treatment phase is based on the dose variation parameter.

15. The system according to claim 10, wherein the gated image data is 4D-computed tomography (CT) image data.

16. The system according to claim 10, wherein the optimal treatment phase is for all of the one or more defined regions.

17. The system according to claim 10, wherein the one or more dose parameters for each region includes a dose variation parameter that corresponds to a starting phase of a dose variation in a sinusoidal pattern, and wherein the optimal treatment phase is based on the dose variation parameter.

18. A non-transitory computer-readable storage medium storing instructions for determining optimal treatment information for a patient, the instructions comprising:

processing treatment plan information for a patient to determine a deformation parameter, the treatment plan information including gated image data of the patient for a plurality of phases with one or more defined target regions and treatment plan dose distribution associated with the one or more defined target regions, the deformation parameter representing a movement of each region due to respiration at different phases;

determining a dose distribution for the one or more target regions by applying the deformation parameter to the treatment plan dose distribution for a subset of the plurality of phases;

determining one or more dose parameters based on the dose distribution for the subset of the plurality of phases, the one or more dose parameters representing a motion of the dose distribution over the plurality of phases for each region; and determining optimal treatment information for the patient based on the one or more dose parameters, the optimal treatment information including an optimal treatment phase and associated dose distribution for each region during the optimal treatment phase, the optimal treatment phase being a phase of the plurality of phases having a minimum total dose for the one or more target regions.

19. The medium according to claim 18, wherein the gated image data is 4D-computed tomography (CT) image data.

20. The medium according to claim 18, wherein the optimal treatment phase is for all of the one or more defined regions.

* * * * *